(12) United States Patent
Majeti et al.

(10) Patent No.: US 12,194,093 B2
(45) Date of Patent: *Jan. 14, 2025

(54) DOSING PARAMETERS FOR CD47 TARGETING THERAPIES TO HEMATOLOGIC MALIGNANCIES

(71) Applicants: The Board of Trustees of the Leland Stanford Junior University, Stanford, CA (US); Forty Seven, LLC, Foster City, CA (US)

(72) Inventors: Ravindra Majeti, Palo Alto, CA (US); Mark Ping Chao, Palo Alto, CA (US); Jie Liu, Palo Alto, CA (US); Jens-Peter Volkmer, Menlo Park, CA (US); Irving L. Weissman, Stanford, CA (US)

(73) Assignees: The Board of Trustees of the Leland Stanford Junior University, Stanford, CA (US); Forty Seven, LLC, Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/143,978

(22) Filed: May 5, 2023

(65) Prior Publication Data

US 2023/0270852 A1 Aug. 31, 2023

Related U.S. Application Data

(62) Division of application No. 17/468,265, filed on Sep. 7, 2021, which is a division of application No. 16/619,387, filed as application No. PCT/US2018/038798 on Jun. 21, 2018, now Pat. No. 11,141,480.

(60) Provisional application No. 62/523,182, filed on Jun. 21, 2017.

(51) Int. Cl.
| | | |
|---|---|---|
| *A61P 35/02* | (2006.01) | |
| *A61K 31/17* | (2006.01) | |
| *A61K 39/395* | (2006.01) | |
| *A61K 45/06* | (2006.01) | |
| *C07K 16/28* | (2006.01) | |
| *A61K 39/00* | (2006.01) | |

(52) U.S. Cl.
CPC .......... *A61K 39/3955* (2013.01); *A61K 31/17* (2013.01); *A61K 45/06* (2013.01); *A61P 35/02* (2018.01); *C07K 16/2803* (2013.01); *A61K 2039/505* (2013.01); *A61K 2039/545* (2013.01); *C07K 2317/24* (2013.01)

(58) Field of Classification Search
CPC .... A61K 39/3955; A61K 31/17; A61K 45/06; A61K 2039/505; A61K 2039/545; A61P 35/02; C07K 16/2803; C07K 2317/24
USPC ..................................................... 424/133.1
See application file for complete search history.

(56) References Cited

U.S. PATENT DOCUMENTS

| | | |
|---|---|---|
| 8,562,997 B2 | 10/2013 | Jaiswal et al. |
| 8,758,750 B2 | 6/2014 | Weissman et al. |
| 9,396,682 B2 | 7/2016 | Xia et al. |
| 9,399,682 B2 | 7/2016 | Jaiswal et al. |
| 9,493,575 B2 | 11/2016 | Jaiswal et al. |
| 9,623,079 B2 | 4/2017 | Willingham et al. |
| 9,796,781 B2 | 10/2017 | Majeti et al. |
| 10,301,387 B2 | 5/2019 | Willingham et al. |
| 11,136,391 B2 | 10/2021 | Willingham et al. |
| 11,141,480 B2 * | 10/2021 | Majeti ............... A61P 35/02 |
| 11,518,806 B2 | 12/2022 | Willingham et al. |
| 11,603,404 B2 | 3/2023 | Willingham et al. |
| 2010/0080769 A1 | 4/2010 | Grillo-Lopez et al. |

(Continued)

FOREIGN PATENT DOCUMENTS

| | | |
|---|---|---|
| CN | 102639565 A | 8/2012 |
| WO | WO-2011/021014 A2 | 2/2011 |
| WO | WO-2014/123580 A1 | 8/2014 |

(Continued)

OTHER PUBLICATIONS

Boasman, K. et al., Role of Pro-Phagocytic Calreticulin and Anti-Phagocytic CD47 in MDS and MPN Models Treated With Azacytidine or Ruxolitinib, Euro. Hema. Assoc., Abstract, 2 pages (2017). <https://library.ehaweb.org/eha/2017/22nd/182624/kristian.boasman.role.of.pro-phagocytic.calreticulin.and.anti-phagocytic.cd47.html>.

(Continued)

*Primary Examiner* — Yan Xiao
(74) *Attorney, Agent, or Firm* — Choate, Hall & Stewart LLP; Rolando Medina; Melissa Adams

(57) ABSTRACT

Methods are provided herein for determining and administering optimized dosing of therapeutic anti-CD47 agents, in a schedule that provides safe escalation of dose while achieving a therapeutic level in a clinically effective period of time. The methods can comprise the steps of clearance, escalation, and maintenance. In one embodiment the dosing regimen administers an initial (i) sub-therapeutic dose of an anti-CD47 agent or (ii) a cytoreductive therapy to achieve a safe level of circulating tumor cells for subsequent treatment (clearance); escalating the dose of an anti-CD47 agent until a therapeutic dose is reached (escalation); and maintaining the therapeutic dose for a period of time sufficient to reduce tumor cells in the bone marrow of the patient (maintenance). In an alternative dosing regimen, a patient determined to have a safe level of circulating tumor cells at presentation is treated by the steps of escalation and maintenance without initial clearance.

6 Claims, 9 Drawing Sheets

(56) References Cited

U.S. PATENT DOCUMENTS

| | | | |
|---|---|---|---|
| 2016/0008429 | A1 | 1/2016 | Willingham et al. |
| 2016/0094698 | A1 | 3/2016 | Lee et al. |

FOREIGN PATENT DOCUMENTS

| | | |
|---|---|---|
| WO | WO-2014/149477 A1 | 9/2014 |
| WO | WO-2015/041987 A1 | 3/2015 |
| WO | WO-2016/094698 A1 | 6/2016 |
| WO | WO-2017/053423 A1 | 3/2017 |

OTHER PUBLICATIONS

Fischer, K. et al., Venetoclax and obinutuzumab in chronic lymphocytic leukemia, Blood, 129(19):2702-2705 (2017).

Li, B, Research progress of cytarabine combined with interferon in the treatment of leukemia, Guangdong Chemical Industry, 42:109-131 (2015).

Métayer, L. E. et al., Anti-CD47 antibodies induce phagocytosis of live, malignant B cells by macrophages via the Fc domain, resulting in cell death by phagoptosis, Oncotarget, 8(37):60892-60903 (2017).

Sallman, D et al., The First-In-Class Anti-CD47 Antibody HU5F9-G4 Is Active And Well Tolerated Alone Or In Combination With Azacitidine In AML And MDS Patients: Initial Phase 1B Results, 24th Congress Euro. Hema. Assoc., Abstract, S878:394 (2019).

Triozzi, P. L. et al., Differential effects of low-dose decitabine on immune effector and suppressor responses in melanoma-bearing mice, Cancer Immunol Immunother, 61:1441-1450 (2012).

Zhang, M. et al., Phagocytosis of Glioblastoma by M1 and M2 Polarized Macrophages and Promotes M1 Polartized Macrophages In Vivo, PLOS One, 11(4):1-21 (2016).

Clinical Trials: NCT04435691, Magrolimab, Azacitidine, and Venetoclax for the Treatment of Acute Myeloid Leukemia, 19 pages, First Submitted Jun. 15, 2020, <https://classic.clinicaltrials.gov/ct2/show/NCT04435691>.

Clinical Trials: NCT04778397, Study of Magrolimab in Combination With Azacitidine Versus Physician's Choice of Venetoclax in Combination With Azacitidine or Intensive Chemotherapy in Patients With TP53 Mutant Acute Myeloid Leukemia That Have Not Been Treated (ENHANCE-2), 20 pages, First Submitted Feb. 23, 2021, <https://classic.clinicaltrials.gov/ct2/show/NCT04778397>.

Clinical Trials: NCT05079230, Study of Magrolimab Versus Placebo in Combination With Venetoclax and Azacitidine in Participants With Acute Myeloid Leukemia, 15 pages, First Submitted Oct. 4, 2021, <https://clinicaltrials.gov/study/NCT05079230?tab=history&a=4>.

Font, P., Azacitidine for the treatment of patients with acute myeloid leukemia with 20%-30% blasts and multilineage dysplasia, Adv Ther, vol. 28, Abstract (2011).

Liu, J. et al., Pre-Clinical Development of a Humanized Anti-CD47 Antibody with Anti-Cancer Therapeutic Potential, PLoS One, 10(9):1-23 (2015).

Misaghian, N. et al., Targeting the leukemic stem cell: the holy grail of leukemia therapy, Leukemia, 25-42 (2008).

Sutherland, M. S. et al., 5-azacytidine enhances the anti-leukemic activity of lintuzumab (SGN-33) in preclinical models of acute myeloid leukemia, MAbs, 2(4):440-8 (2010).

Clinical Trials: NCT04313881, Magrolimab + Azacitidine Versus Azacitidine + Placebo in Untreated Participants With Myelodysplastic Syndrome (Mds) (Enhance), 15 pages, Study Start: Jan. 9, 2020, <https://classic.clinicaltrials.gov/ct2/show/NCT04313881>.

Daver, N. G. et al., Tolerability and Efficacy of the Anticluster of Differentiation 47 Antibody Magrolimab Combined With Azacitidine in Patients With Previously Untreated AML: Phase lb Results, Jrnl. Clin. Oncol., 41(31): 4893-4906 (2023).

Gilead, Gilead Statement on the Discontinuation of Magrolimab Study in AML with TP53 Mutations, Press Release (Sep. 26, 2023) <https://www.cancertherapyadvisor.com/home/cancer-topics/hematologic-cancers/hematologic-cancers-news/study-evaluating-magrolimab-in-patients-with-tp53-mutant- aml-discontinued/# :~: text=The%20decision%20to%20discontinue%20the,was%20similar%20betw een%20the %20groups>.

Gilead, Gilead To Discontinue Phase 3 ENHANCE Study of Magrolimab Plus Azacitidine in Higher-Risk MDS, Press Release, 4 pages (Jul. 21, 2023) <https://www.gilead.com/news-and-press/press-room/press-releases/2023/7/gilead-to-discontinue-phase-3-enhance-study-of-magrolimab-plus-azacitidine-in-higher-risk-mds>.

Sallman, D. A. et al., Magrolimab in Combination With Azacitidine in Patients With Higher- Risk Myelodysplastic Syndromes: Final Results of a Phase Ib Study, Jrnl. Clin. Oncol., 1-14 (2023).

Clinical Trials: NCT04313881, Magrolimab + Azacitidine Versus Azacitidine + Placebo in Untreated Participants With Myelodysplastic Syndrome (Mds) (Enhance), 15 pages, Study Start Sep. 9, 2020 <https://www.clinicaltrials.gov/study/NCT04313881>.

Gilead, Enhance Magrolimab Trial Summary, 4 pages posted Feb. 26, 2024.

Gilead, Statement on Discontinuation of Phase 3 ENHANCE-3 Study in AML, 4 pages, Posted Feb. 27, 2024, <https://www.gilead.com/news-and-press/company-statements/gilead-statement-on-discontinuation-of-phase-3-enhance-3-study-in-aml# :~: text=(Nasdaq%3A%20GILD)%20today%20announced,programs%2C%20on%20full%20clini cal%20hold.>.

Qu, T. et al., Ligufalimab, a novel anti-CD47 antibody with No. hemagglutination demonstrates both monotherapy and combo antitumor activity, J. Immunother. Cancer, 10:1-12 (2022).

Sikic, B. I. et al., First-in-Human, First-in-Class Phase l Trial of the Anti-CD47 Antibody Hu5F9-G4 in Patients With Advanced Cancers, Jrnl. Clin. Onco., 37(12): 946-953 (2019).

* cited by examiner

FIG. 5
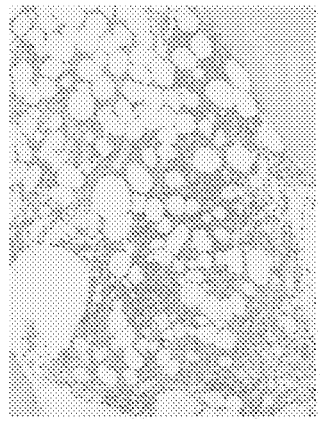
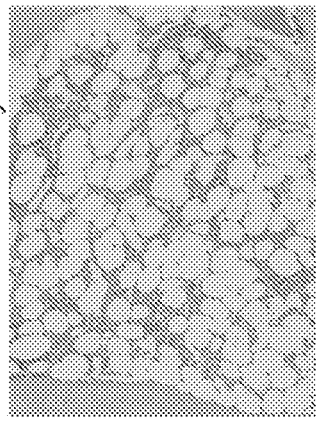
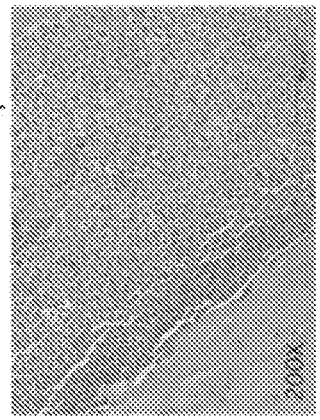
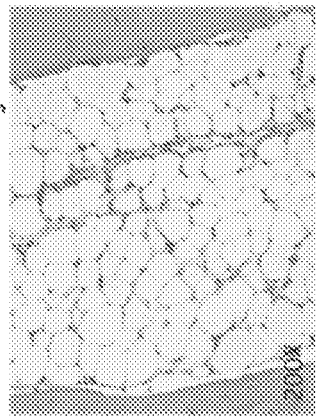

FIG. 8

Hu5F9-G4 AML dosing profile range: Phase 1 AML trial

| Cohort | Week 1 | | Week 2 | | | Week 3 | | | Week 4 | | | Week 5+ |
|---|---|---|---|---|---|---|---|---|---|---|---|---|
| | D1 | D4 | D8 | D11 | D15 | D18 | D22 | D25 | D29+ |
| 1 | 0.1 mg/kg | 0.1 mg/kg | 0.3 mg/kg | 0.3 mg/kg | 1 mg/kg | 1 mg/kg | 1 mg/kg | 1 mg/kg | 1 mg/kg twice weekly |
| 2 | 0.3 mg/kg | 0.3 mg/kg | 1 mg/kg | 1 mg/kg | 3 mg/kg | 3 mg/kg | 3 mg/kg | 3 mg/kg | 3 mg/kg twice weekly |
| 3 | 1 mg/kg | 1 mg/kg | 3 mg/kg | 3 mg/kg | 10 mg/kg | 10 mg/kg | 10 mg/kg | 10 mg/kg | 10 mg/kg twice weekly |
| 4 | 1 mg/kg | 1 mg/kg | 10 mg/kg | 10 mg/kg | 15 mg/kg | 15 mg/kg | 15 mg/kg | 15 mg/kg | 15 mg/kg twice weekly |
| 5 | 1 mg/kg | 1 mg/kg | 15 mg/kg | 30 mg/kg | 30 mg/kg | 30 mg/kg | 30 mg/kg | 30 mg/kg | 30 mg/kg twice weekly |

Therapeutic Dosing Profile

| Week 1 | | Week 2 | | Week 3 | | Week 4 | | Week 5+ |
|---|---|---|---|---|---|---|---|---|
| D1 | D4 | D8 | D11 | D15 | D18 | D22 | D25 | D29+ |
| 1 mg/kg | 1 mg/kg | 15 mg/kg | 30 mg/kg | 30 mg/kg | 30 mg/kg | 30 mg/kg | 30 mg/kg | 30 mg/kg twice weekly |
| 1 mg/kg | 1 mg/kg | 30 mg/kg | 60 mg/kg | 60 mg/kg | 60 mg/kg | 60 mg/kg | 60 mg/kg | 60 mg/kg twice weekly |

DOSING PARAMETERS FOR CD47 TARGETING THERAPIES TO HEMATOLOGIC MALIGNANCIES

CROSS REFERENCE TO RELATED APPLICATIONS

This application is a divisional of U.S. application Ser. No. 17/468,265 filed Sep. 7, 2021, which is a divisional of U.S. application Ser. No. 16/619,387 filed Dec. 4, 2019, now U.S. Pat. No. 11,141,480, which is a National Stage Entry under 35 U.S.C. § 371 of International Application No. PCT/US2018/038798 filed Jun. 21, 2018, which claims benefit under 35 U.S.C. § 119(e) of U.S. Provisional Application No. 62/523,182 filed Jun. 21, 2017, the contents of each of these applications are incorporated herein by reference in their entireties.

BACKGROUND

CD47 is a broadly expressed transmembrane glycoprotein with a single Ig-like domain and five membrane spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells. CD47 mediates a variety of biological processes, including leukocyte adhesion and migration, T-cell activation, apoptosis and phagocytosis.

SIRPα inhibits the phagocytosis of host cells by macrophages, where the ligation of SIRPα on macrophages by CD47 expressed on the host target cell generates an inhibitory signal mediated by SHP-1 that negatively regulates phagocytosis. SIRPα acts to detect signals provided by "self," to negatively control innate immune effector function against these cells.

CD47 is also constitutively upregulated on a number of cancers, including leukemias. Overexpression of CD47 increases pathogenicity by allowing the cancer cells to evade phagocytosis. Although targeting CD47 represents a unique mechanism of action for treatment of cancer, the widespread expression of CD47 presents a therapeutic challenge. In addition, treatment of leukemias and related hematologic disorders presents special problems, including the adverse effects of the cancer on bone marrow and hematologic function, and complications from tumor lysis syndrome. The methods provided herein address these challenges.

SUMMARY OF THE INVENTION

Hematologic malignancies, including without limitation leukemias such as acute myeloid leukemia, acute lymphocytic leukemia, multiple myeloma, etc., pose a unique set of problems for effective therapy. If killed too quickly, the high burden of circulating tumor cells often associated with leukemias can be toxic to the patient. This can be a risk with escalating the dose of an anti-CD47 agent too quickly. At the same time, it is desirable to bring a patient up to therapeutic levels of the agent as quickly to provide therapeutic benefit.

Methods are provided herein for determining and administering optimized dosing of therapeutic anti-CD47 agents, in a schedule that provides safe escalation of dose while achieving a therapeutic level in a clinically effective period of time. The methods can comprise the steps of clearance, escalation, and maintenance. In one embodiment the dosing regimen administers an initial (i) sub-therapeutic dose of an anti-CD47 agent or (ii) a cytoreductive therapy to achieve a safe level of circulating tumor cells for subsequent treatment (clearance); escalating the dose of an anti-CD47 agent until a therapeutic dose is reached, in which greater than about 80% receptor occupancy is achieved in bone marrow blast cells from the patient (escalation); and maintaining the therapeutic dose for a period of time sufficient to reduce tumor cells in the bone marrow of the patient (maintenance). In an alternative dosing regimen, a patient determined to have a safe level of circulating tumor cells at presentation is treated by the steps of escalation and maintenance, comprising: escalating the dose of an anti-CD47 agent until a therapeutic dose is reached, in which greater than about 80% receptor occupancy is achieved in bone marrow blast cells from the patient (escalation); and maintaining the therapeutic dose for a period of time sufficient to reduce tumor cells in the bone marrow of the patient (maintenance).

The parameters for the dose and timing can be included in a "ramp" schedule, which provides both general guidelines for administration, and specific points at which individual patient data can be utilized for adjusting the ramp, for example by evaluating the level of circulating blast cells; by monitoring the receptor occupancy of bone marrow blast cells; etc.

The high circulating and bone marrow tumor burden associated with hematologic malignancies can create toxicity issues when an individual is administered a therapeutic dose of an anti-CD47 agent without suitable dose escalation, in addition to the effect of anti-CD47 treatment on erythrocytes. The toxicity may result from lysis of circulating tumor cells. In the present methods, escalation to a therapeutic level is not initiated until the patient has a safe level of circulating tumor cells, which state may be referred to as the escalation point. Reaching a safe level, if the initial circulating tumor cell levels are too high, can be achieved by administering a cytoreductive agent, e.g. hydroxyurea, hydroxycarbamide, fludarabine, oral etoposide, leukapheresis, etc. to reduce the circulating tumor cell burden. Alternatively this can be achieved by administering a low, sub-therapeutic level of the anti-CD47 agent. Once a safe level of circulating cells is reached, then the dose can be escalated to therapeutic levels. This dose escalation prevents early mortality and provides for safe clearance of leukemic cells.

In some embodiments, a therapeutic dose for treatment of hematologic malignancies is equivalent to a dose that provides for substantially complete occupancy of CD47 binding sites on the surface of blast cells in bone marrow by an anti-CD47 agent (referred to herein as receptor occupancy), for a defined period of time. In some embodiments the anti-CD47 agent specifically binds to CD47. Substantially complete receptor occupancy may be at least about 75%, at least about 80%, at least about 85%, at least about 90%, at least about 95%, at least about 98%, or more. The defined period of time may be, for example, the time between dose administration, e.g. around 1 day, around 2 days, around 4 days, around 4 days, around 5 days, around 6 days, around 1 week, around 10 days, around 2 weeks, and the like. Alternatively the defined period of time may be the time between administration of a therapeutic dose and transplantation, between administration of a therapeutic dose and administration of an alternative, complementary, and/or synergistic additional agents, and the like.

The dosing schedule for an anti-CD47 agent of interest can include (i) the number of escalations, e.g. 1, 2, 3, 4, 5, 6, 7, 8, 9, 10, etc.; (ii) the period of time between escalations, e.g. around 1 day, around 2 days, around 4 days, around 4 days, around 5 days, around 6 days, around 1 week, around 10 days, around 2 weeks, and the like; (iii) the level of increase in dose for each escalation, and whether fixed or variable; and (iv) the initial dose. A schedule may also include (v) dosing and/or escalation of a cytoreductive agent to reduce the circulating tumor cell burden. These parameters define a schedule for safe and clinically efficacious dosing.

Data points for assessment of an individual response and adjustment of the schedule may include determining the number of circulating tumor cells; and determining whether an individual has reached a therapeutic level of an anti-CD47 agent, e.g. by determining the receptor occupancy of CD47 binding sites on the surface of tumor cells, e.g. in bone marrow or in blood; determining serum level of the anti-CD47 agent, etc.

To determine the number of circulating tumor cells, measurement can be made of circulating blast cells, or of white blood cells, where the term "blast cell" is used to refer to circulating hematologic tumor cells. In some embodiments, when patient circulating blast cells are greater than about $20 \times 10^9$/liter, greater than about $15 \times 10^9$/liter, greater than about $10 \times 10^9$/liter, greater than about $5 \times 10^9$/liter, greater than about $2 \times 10^9$/liter the patient is treated with a sub-therapeutic dose of an anti-CD47 agent, treated with a cytoreductive agent, or both, until such time as the level of circulating blast cells is reduced to a safe level for therapy. Conversely, a patient with initial levels of less than about $2 \times 10^9$/liter circulating blast cells, less than about $5 \times 10^9$/liter, less than about $10 \times 10^9$/liter can be started at the escalation step without cytoreduction. Circulating white blood cells (WBC) can be counted instead of circulating blast cells, where when patient circulating WBC are greater than about $50 \times 10^9$/liter, greater than about $20 \times 10^9$/liter, greater than about $5 \times 10^9$/liter the patient is treated with a sub-therapeutic dose of an anti-CD47 agent, treated with a cytoreductive agent, or both, until such time as the level of circulating tumor cells is reduced to a safe level for therapy. Conversely, a patient with initial levels of less than about $5 \times 10^9$/liter circulating WBC cells, less than about $10 \times 10^9$/liter, less than about $20 \times 10^9$/liter can be started at the escalation step without cytoreduction.

The methods include administration of an anti-CD47 agent for the treatment of hematologic malignancies in combination therapies, which may provide for an additive and/or synergistic effect in the reduction of tumor cells. Specific combination therapies include, without limitation, combinations with cytoreductive agents and therapies, combinations with hypomethylating (epigenetic) agents, combinations with immuno-oncology agents, including those agents that act on T cells, combinations with tumor-targeted agents, for example antibodies that selectively bind to cancer cell markers, combinations with biologic factors that increase phagocytic cell activation, growth, localization and the like; combination with transplantation, transfusion, leukapheresis, erythropoietin stimulating agents including erythropoietin, and the like.

The methods include patient selection for efficacy of an anti-CD47 agent for the treatment of hematologic malignancies and treatment of selected patients. Selection criteria may be based on clinical parameters, expression of biomarkers, and the like. Included as biomarkers are molecular mutations for enrichment of efficacy, e.g. MDS-specific mutations. Clinical parameters may include, without limitation, intermediate/high risk MDS patients (R/R); combination therapy with azacitidine for treatment naïve unfit patients; monotherapy for patients ineligible for induction chemotherapy who are relapsed/refractory to conventional therapies; and treatment of patients with minimal residual disease.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 5. Photomicrographs of Bone Marrow Biopsies from Mice and Patients Treated with Anti-CD47 Ab (Mice: Clone B6H12; Human: Clone Hu5F9-G4).

FIG. 8. Clinical dosing profile.

DETAILED DESCRIPTION

Figure 1:
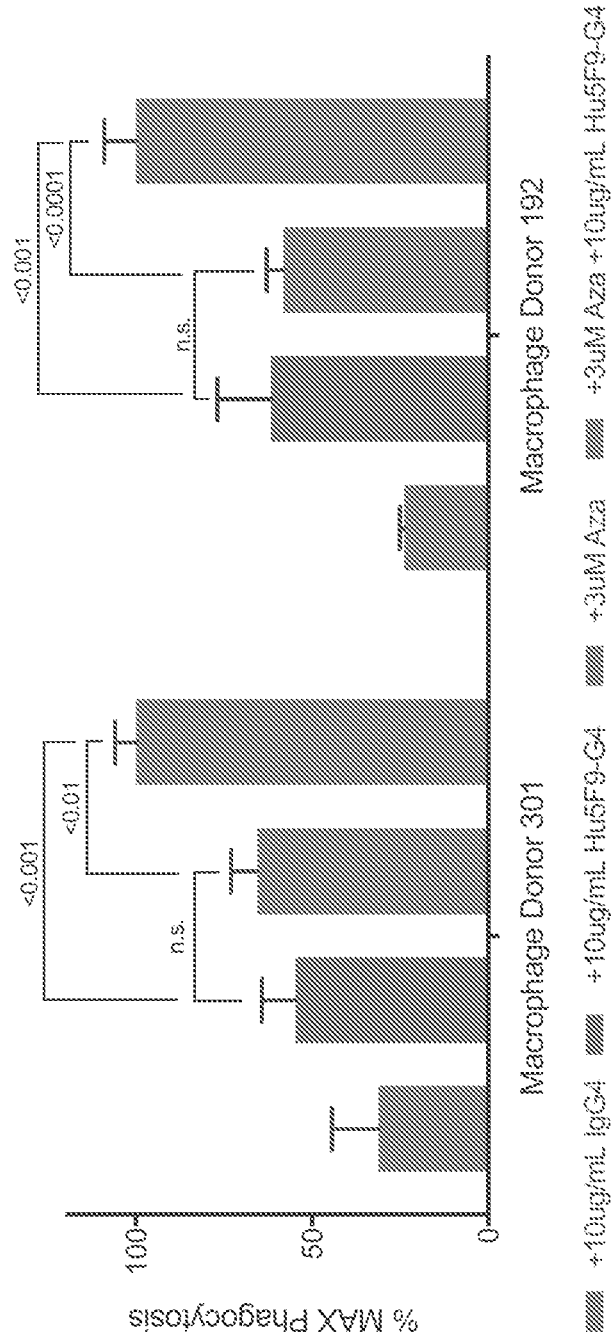
FIG. 1. Enhanced Macrophage Phagocytosis of Acute Myelogenous Leukemia Cells by Combination Treatment of Hu5F9-G4 with Azacitidine. Abbreviation: AZA=Azacitidine.

Methods are provided for determining and administering optimized dosing of therapeutic anti-CD47 agents for treatment of hematologic malignancies, e.g. leukemias, in a schedule that provides safe escalation of dose while achieving a therapeutic level in a clinically effective period of time.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Usually, the mammal is human.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

The terms "hematological malignancy", "hematological tumor", and "hematological cancer" are used interchangeably and in the broadest sense herein and refer to all stages and all forms of cancer arising from cells of the hematopoietic system.

Examples of hematologic malignancies that may be treated using the subject methods include leukemias, lymphomas, and myelomas, including but not limited to acute biphenotypic leukemia, acute myelogenous leukemia (AML), acute lymphoblastic leukemia (ALL), acute promyelocytic leukemia (APL), biphenotypic acute leukemia (BAL) blastic plasmacytoid dendritic cell neoplasm, chronic myelogenous leukemia (CML), chronic myelomonocytic leukemia (CMML), chronic lymphocytic leukemia (CLL) (called small lymphocytic lymphoma (SLL) when leukemic cells are absent), acute monocytic leukemia (AMOL), Hodgkin's lymphomas, Non-Hodgkin's lymphomas (e.g. chronic lymphocytic leukemia (CLL), diffuse large B-cell lymphoma (DLBCL), Follicular lymphoma (FL), Mantle cell lymphoma (MCL), Marginal zone lymphoma (MZL), Burkitt's lymphoma (BL), Hairy cell leukemia, Post-transplant lymphoproliferative disorder (PTLD), Waldenström's macroglobulinemia/lymphoplasmacytic lymphoma, hepatosplenic-T cell lymphoma, and cutaneous T cell lymphoma (including Sezary's syndrome)), multiple myeloma, myelodysplastic syndrome, and myeloproliferative neoplasms. In particular embodiments, the subject methods find utility in treatment of leukemias, e.g. acute biphenotypic leukemia, acute myelogenous leukemia (AML), acute lymphoblastic leukemia (ALL), acute promyelocytic leukemia, chronic myelogenous leukemia (CML), chronic myelomonocytic leukemia, chronic lymphocytic leukemia (CLL), acute monocytic leukemia (AMOL).

For AML, various molecular markers can find use in patient selection and dosing, including without limitation known clinical prognostic factors associated with favorable outcome include cytogenetic mutations such as t(15;17) PML/RARα, t(8;21)AML1/ETO, 11q23, and inv(16)CBFβ/MYH11, or molecular mutations in FLT3 associated with intermediate risk (e.g., FLT3-ITD, FLT3-D835), NPM1, EVI1, or cEBPα; clinical prognostic factors that have been associated with an intermediate outcome include but are not limited to normal karyotype, and the cytogenetic mutations +8, +21, +22, del(7q), and del(9q); and clinical prognostic factors that have been associated with an adverse outcome include but not limited to the cytogenetic mutations del(5q), 11q23, t(6;9), t(9;22), abnormal 3q, complex cytogenetics, and elevated expression levels of IL2Ra and/or MSI2.

As used herein, a "target cell" is a hematologic malignant cell expressing CD47 on the surface, where masking or otherwise altering the CD47 positive phenotype (e.g., by administration of an anti-CD47 agent) results in increased phagocytosis. Usually a target cell is a mammalian cell, for example a human cell.

Circulating and bone marrow blast cells. It is typical of leukemias and myelodysplastic syndromes that tumor cells are found in the circulation and bone marrow. The number of blast cells, or white blood cells can be counted in these tissues. Counting blast cells can be more accurate, as the percentage of WBC that are blasts can vary with the condition.

The French-American-British (FAB) classification requires a blast percentage of at least 30% in bone marrow (BM) or peripheral blood (PB) for the diagnosis of acute myeloid leukemia (AML), and also requires specific blast percentages to subclassify MDS. In contrast, the World Health Organization (WHO) classification decreases the cutoff limit for the diagnosis of AML from 30 to 20% BM or PB blasts. The percentage of PB and BM blasts is not as important for the diagnosis of acute lymphoblastic leukemia (ALL), because the presence of any clonal blast population is diagnostic. However, post-therapy PB blast percentage is an important prognostic index that reflects the outcome in ALL.

The diagnosis of leukemia and MDS is based on BM blasts because, in most cases, the percentage of blasts is higher in BM than in PB. In a small proportion of patients with acute leukemia known as 'peripheral leukemia,' however, there is no diagnostic increase in BM blast percentage; the diagnosis is based on the presence of at least 20% PB blasts. In addition to the blast percentage, numbers of circulating blasts can provide a useful measure.

The escalation point, or the point at which it is safe to initiate an escalation of the anti-CD47 agent to therapeutic levels, may be defined by the level of circulating blast cells or WBC. In some methods the number is monitored at one or more time points to determine whether it is appropriate to initiate dose escalation to therapeutic levels. The escalation point can be, for example, less than about $2 \times 10^9$/liter circulating blast cells, less than about $5 \times 10^9$/liter, less than about $10 \times 10^9$/liter or for white blood cells (WBC) less than about $5 \times 10^9$/liter circulating WBC cells, less than about $10 \times 10^9$/liter, less than about $20 \times 10^9$/liter.

Cytoreductive therapy is the process by which the number of circulating blast cells are reduced, e.g. to reach the escalation point. For example, a patient having circulating blast cells greater than about $20 \times 10^9$/liter, greater than about $15 \times 10^9$/liter, greater than about $10 \times 10^9$/liter, etc. is treated with a cytoreductive therapy to reduce the number of circulating blast cells.

One cytoreductive therapy of interest is the administration of a sub-therapeutic dose of an anti-CD47 agent. A sub-therapeutic dose is a dose (i.e., an amount) that prevents sudden death from tumor cell lysis, agglutination etc. A sub-therapeutic dose of an anti-CD47 agent can depend on the specific agent used, but may be the dose equivalent to less than about 20 mg/kg of 5F9G4 antibody, less than about 15 mg/kg of 5F9G4 antibody, less than about 10 mg/kg of 5F9G4 antibody, less than about 7.5 mg/kg of 5F9G4 antibody, less than about 5 mg/kg of 5F9G4 antibody, less than about 2.5 mg/kg of 5F9G4 antibody, less than about 1 mg/kg of 5F9G4 antibody. A sub-therapeutic dose may be, for example, equivalent to from about 1-20 mg/kg of 5F9G4 antibody, from about 2.5 to about 15 mg/kg of 5F9G4 antibody, from about 5-10 10 mg/kg of 5F9G4 antibody.

Alternative methods for cytoreduction utilize administration of a cytoreductive agent other than an anti-CD47 agent, for example hydroxyurea, hydroxycarbamide, fludarabine, oral etoposide, leukapheresis, etc. Such agents are administered in accordance with known methods, for example hydroxyurea can be administered at a dose of from about 10, about 15, about 20, about 25, about 30 mg/kg PO per day, or in flat doses of a minimum of 500 mg PO daily to up to 6 grams PO daily.

A "therapeutically effective dose" or "therapeutic dose" is an amount sufficient to effect desired clinical results (i.e., achieve therapeutic efficacy). For purposes of this invention, a therapeutically effective dose of an anti-CD47 agent is an amount that is sufficient to palliate, ameliorate, stabilize, reverse, prevent, slow or delay the progression of the disease state by increasing phagocytosis of a target cell (e.g., a target cell); for example to reduce the number of tumor cells in the blood, bone marrow, etc. Thus, a therapeutically effective dose of an anti-CD47 agent reduces the binding of CD47 on an target cell, to SIRPα on a phagocytic cell, at an effective dose for increasing the phagocytosis of the target cell.

Target-mediated elimination pathway involves interaction between an anti-CD47 agent and its pharmacological target, and represents a route of protein clearance. For example, binding of mAb on targets on cell surfaces may trigger internalization of the complex into the cells followed by subsequent lysomal degradation of the complex. The target-mediated elimination is saturable because of the finite amounts of target antigen, which may lead to non-linear elimination. Typically, clearance of mAb that binds to membrane antigen is faster at low doses as the unbound targets will "sop up" antibody, serving as a sink (this phenomenon is referred to as the "antigen sink"). Also, changes in the number of targets as a result of the effect of the anti-CD47 agent on erythrocytes and cancer cells alters the pharmacokinetics of therapeutic antibodies through target-mediated elimination pathways.

As an indicator for a therapeutically effective dose, which takes into account the complex interplay between antigen sink, biological activities of the agent and requirement for enhancing phagocytosis of cancer cells, the therapeutic dose can be determined as equivalent to a dose that provides for substantially complete occupancy of CD47 binding sites on the surface of blast cells, e.g. in bone marrow, blood, etc. by an anti-CD47 agent (referred to herein as receptor occupancy), for a defined period of time. In some embodiments the anti-CD47 agent specifically binds to CD47. Substantially complete receptor occupancy may be at least about 75%, at least about 80%, at least about 85%, at least about 90%, at least about 95%, at least about 98%, or more.

Figure 7:
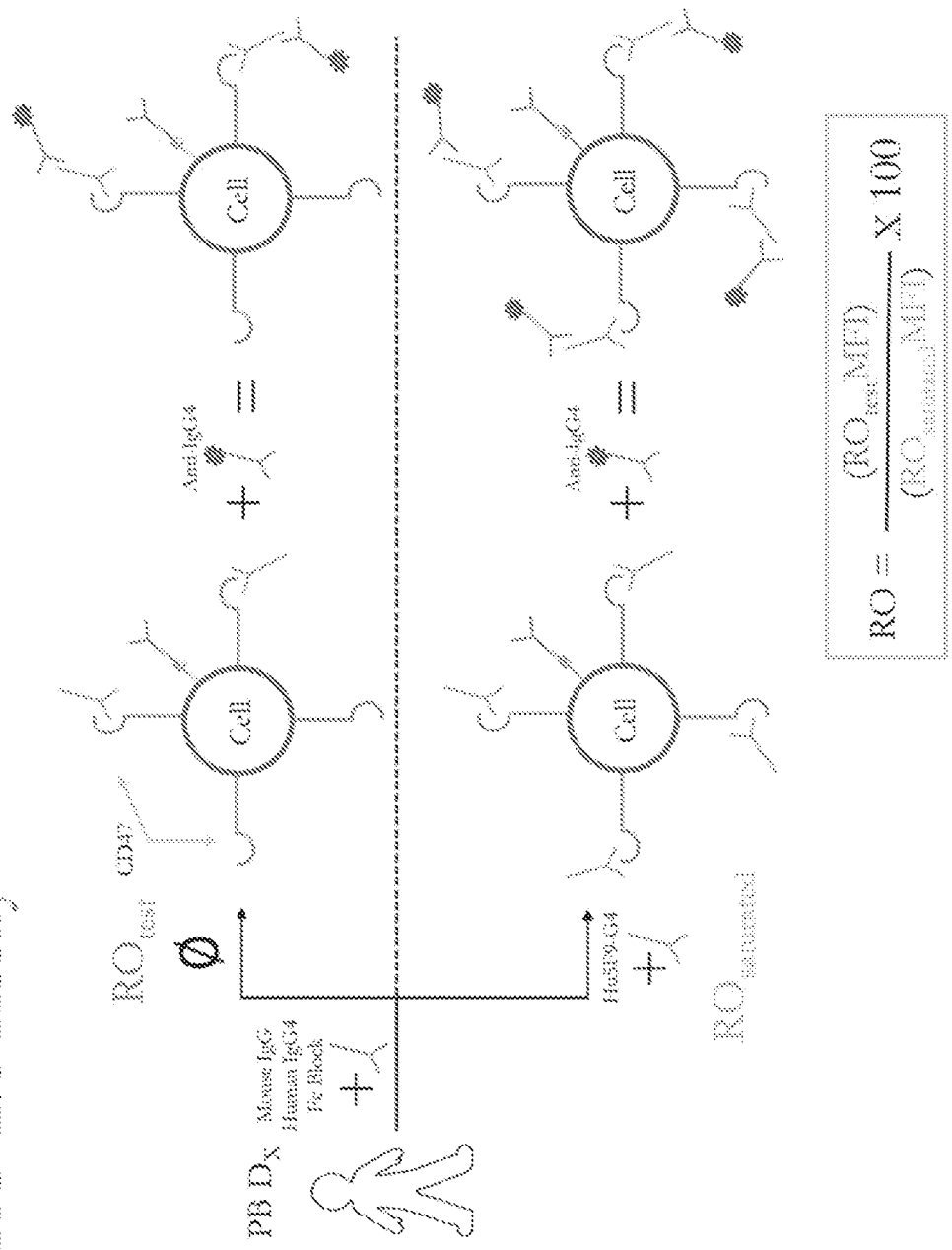
FIG. 7. Schematic of assay for receptor occupancy.

Receptor occupancy can be measured by a competition assay, for example as shown in FIG. 7. For example, after administration of an agent to an individual, a suitable biological sample is obtained, usually a bone marrow aspirate, which is optionally treated to separate WBC from stromal and other cells. The sample is split, where one aliquot is artificially saturated with the anti-CD47 agent. The two aliquots are then stained with a detectably labeled counterpart of the anti-CD47 agent; and the detectable label quantitated. Receptor occupancy is the percentage ratio of the test sample divided by the artificially saturated sample.

Receptor occupancy can transiently peak following administration of the agent, and therefore it is useful to define the period of time for which substantially complete receptor occupancy is achieved. The defined period of time may be, for example, the time between dose administration, e.g. around 1 day, around 2 days, around 4 days, around 4 days, around 5 days, around 6 days, around 1 week, around 10 days, around 2 weeks, and the like. Alternatively the defined period of time may be the time between administration of a therapeutic dose and transplantation, between administration of a therapeutic dose and administration of an alternative, complementary, and/or synergistic additional agents, and the like. For example, a measurement of receptor occupancy of CD47 in bone marrow blasts can be determined around 1 day, around 2 days, around 4 days, around 4 days, around 5 days, around 6 days, around 1 week, around 10 days, around 2 weeks following administration of a dose of the agent.

As a surrogate for receptor occupancy, the serum levels of the anti-CD47 agent can be determined. In some embodiments, a therapeutically effective dose leads to sustained serum levels of anti-CD47 agent (e.g., an anti-CD47 antibody) of about 40 µg/ml or more (e.g., about 50 µg/ml or more, about 60 µg/ml or more, about 75 µg/ml or more, about 100 µg/ml or more, about 125 µg/ml or more, or about 150 µg/ml or more). In some embodiments, a therapeutically effective dose leads to sustained serum levels of anti-CD47 agent (e.g., an anti-CD47 antibody) that range from about 40 µg/ml to about 300 µg/ml, up to about 500 µg/ml, up to about 750 µg/ml, up to about 1000 µg/ml, e.g, from about 40 µg/ml to about 1000 µg/ml, from about 40 µg/ml to about 800 µg/ml, from about 40 µg/ml to about 700 µg/ml, from about 40 µg/ml to about 600 µg/ml, from about 50 µg/ml to about 500 µg/ml, from about 50 µg/ml to about 750 µg/ml, from about 50 µg/ml to about 300 µg/ml, from about 50 µg/ml to about 250 µg/ml, from about 75 µg/ml to about 1000 g/ml from about 75 µg/ml to about 750 µg/ml, from about 75 µg/ml to about 500 µg/ml, from about 75 µg/ml to about 250 µg/ml, from about 100 µg/ml to about 1000 µg/ml, from about 100 g/ml to about 600 µg/ml, or from about 100 µg/ml to about 300 µg/ml). In some embodiments, a therapeutically effective dose for treating hematologic malignancies leads to sustained serum levels of anti-CD47 agent (e.g., an anti-CD47 antibody) of about 50 µg/ml or more (e.g., sustained serum levels of 75 µg/ml or more; or sustained serum levels that range from about 50 µg/ml to about 150 µg/ml).

Escalation. An "escalation" as used herein is an increase in the dose of the agent, and can vary by the level of increase, e.g. about 10% increase, about 20%, about 30%, about 40%, about 50%, about 60%, about 70%, about 80%, about 90%, about 100%, 2-fold, 2.5-fold, 5-fold or more. The level of increase may be constant, or variable. The effect on an individual can be monitored, for example, by determining the level of circulating blast cells, and the escalation may be adjusted based on the numbers of circulating blast cells.

For example, once a patient is determined to have reached a point where escalation is safe, the dose of the anti-CD47 agent can be increased by about 1 mg/kg/dose, by about 2.5 mg/kg/dose, by about 5 mg/kg/dose, by about 7.5 mg/kg/dose, by about 10 mg/kg/dose; by about 12.5 mg/kg/dose, by about 15 mg/kg/dose, by about 20 mg/kg/dose, by about 25 mg/kg/dose, by about 30 mg/kg/dose, usually from about 1 to about 30 mg/kg/dose, 1-20 mg/kg/dose, 1-15 mg/kg/dose, etc. where the escalation can be weekly, bi-weekly, twice-weekly, semi-weekly, every 3 days, etc.

A "maintenance dose" is a dose that is administered when a therapeutically effective level is reached. A therapeutically effective dose or a series of therapeutically effective doses can achieve and maintain a serum level of anti-CD47 agent, and/or substantially complete receptor occupancy. A therapeutically effective dose of an anti-CD47 agent can depend on the specific agent used, but is usually about 8 mg/kg body weight or more (e.g., about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or about 45 mg/kg or more, or about 50 mg/kg, or about 60 mg/kg or more. Ranges may include from about 10 mg/kg to about 60 mg/kg (e.g., from about 10 mg/kg to about 50 mg/kg, or from about 10 mg/kg to about 30 mg/kg). The dose required to achieve and/or maintain a particular therapeutic dose is proportional to the amount of time between doses and inversely proportional to the number of doses administered. Thus, as the frequency of dosing increases, the required dose decreases. The optimization of dosing strategies will be readily understood and practiced by one of ordinary skill in the art.

Anti-CD47 agent. As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα. The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1 2004). Thus, in some embodiments, the anti-CD47 agent does not directly induce cell death of a CD47-expressing cell.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide (SEQ ID NO:2), such that the extracellular portion of CD47 is typically 142 amino acids in length, and has the amino acid sequence set forth in SEQ ID NO:3. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. In an exemplary embodiment, the CD47 extracellular domain lacking the signal peptide has the amino acid sequence set forth in SEQ ID NO:1 (124 amino acids). As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to a reference CD47 sequence, e.g. Genbank accession number NP_001768.1 or NP_942088.1.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: inhibiting the disease and/or symptom(s), i.e., arresting their development; and/or relieving the disease symptom(s), i.e., causing regression of the disease and/or symptom(s). Those in need of treatment include those already diagnosed with a hematologic malignancy.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-1}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "sample" with respect to a patient encompasses bone marrow, e.g. bone marrow aspirate; blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., cancerous cell, etc.), e.g., a sample comprising polynucleotides and/or polypeptides that is obtained from such cells (e.g., a cell lysate or other cell extract comprising polynucleotides and/or polypeptides). A biological sample comprising tumor cells from a patient can also include non-tumor cells.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

A complete blood count (CBC) and peripheral smear are used to evaluate overall health and detect a wide range of disorders, including anemia, infection and leukemia. A complete blood count test measures several components and features of your blood, including: red blood cells, white blood cells, hemoglobin, hematocrit, platelet count, etc. Abnormal increases or decreases in cell counts as revealed in a complete blood count may indicate an underlying medical condition that calls for further evaluation. Pancytopenia and peripheral blasts suggest acute leukemia. Blast cells in the peripheral smear may approach 100% of WBC count for hematologic malignancies.

The number of blast cells in peripheral blood with infection may be from about $10\text{-}40 \times 10^9/l$, although it may be as high as $100 \times 10^9/l$. In chronic lymphocytic leukemia (CLL) the count is usually substantially raised ($30\text{-}300 \times 10^9/l$), although the diagnosis may be suspected with counts as low as $5\text{-}10 \times 10^9/l$ if their morphological appearance is characteristic.

A blood differential test measures the percentage of each type of white blood cell (WBC) in the blood, and reveals if there are any abnormal or immature cells. Generally the test counts neutrophils; lymphocytes, monocytes, eosinophils and basophils.

To diagnose CLL, a lymphocytosis of greater than 5000/$mm^3$ must be present. The absolute neutrophil count is usually normal and red blood cell counts and platelet counts are mildly decreased. In addition, the peripheral smear or bone marrow should show normal mature small lymphocytes with less than 55% atypical or blast forms.

CML is defined by its peripheral WBC count. Typically, leukocytosis is in excess of 100,000/$mm^3$. The differential count shows that neutrophil precursors are present. This is accompanied by basophilia and eosinophilia. Unlike those in AML, these cells are mature and functional.

AML may be diagnosed by its peripheral WBC count, whereby at least 20% myeloid blasts in the blood signifies a diagnosis of AML.

Bone marrow examination by aspiration or needle biopsy may be routinely done, although the diagnosis can usually be made from the peripheral smear. Blast cells in the bone marrow are classically between 25 and 95% for hematologic malignancies.

Bone marrow aspiration establishes the diagnosis of leukemia. The morphology of blasts usually can differentiate between ALL and AML. In ALL, a homogeneous infiltrate of lymphoblasts replaces the normal bone marrow elements. Lymphoblasts usually are small and measure approximately 14 μm in diameter. They have scant cytoplasm with no granules. The nucleus has no nucleoli or a small indistinct one.

For the diagnosis of AML, at least 20-30% (depending on classification) of the nucleated cells in the aspirate must be blast cells of myeloid origin. Multiple large nucleoli, delicate chromatin, gray-blue cytoplasm, and Auer rods characterize myeloblasts. The presence of Auer rods is virtually diagnostic of AML, because these condensed lysosomal cytoplasmic azurophilic rod-shaped structures do not appear in ALL.

In CLL, bone marrow infiltration exceeds 30% lymphocytes. The lymphocytes are mature with less than 55% atypical or blast forms. The nuclei are round, cytoplasm is scant, chromatin is compact, nucleoli are inconspicuous, and mitotic figures are rare.

Immunophenotyping using multiparameter flow cytometry following labeling with monoclonal antibodies to cell-surface antigens, which identifies the B or T cell origin of the lymphoblasts. Based on the expression of B lineage-restricted antigens and clonal rearrangements of immunoglobulin heavy and light chain genes, it has been estimated that up to 80% of ALL cases arise from B-cell precursors. The majority possesses a common ALL antigen (CALLA) that is present only on leukemic cells. T-cell ALL possesses receptors for sheep erythrocytes, and, when these are combined, they form E-rosettes. Another subset of ALL lacks B- or T-cell characteristics and is referred to as null-cell ALL.

Certain myeloid-specific antigens, such as CD13, CD33, CD41, and others have been used to diagnose AML.

The malignant cells in CLL correspond to a minor subpopulation of B cells that express cell surface immunoglobulin M (IgM) and immunoglobulin D (IgD) and the T-cell associated antigen CD5.

Histochemical stains for myeloperoxidase (Leder stain) and nonspecific esterase have a strong affinity for myelogenous precursors but fail to stain lymphocytic forerunners. Demonstration of nuclear DNA polymerizing enzyme terminal deoxynucleotidyl transferase (TdT) is indicative of a lymphoid origin. However, up to 2-5% of patients with AML exhibit this enzyme. Exceptions may occur when a malignant clone arises from multipotent cells that may express both myelogenous characteristics and lymphocytic characteristics.

Chromosomal analysis also plays an important role. The diagnosis of CML is established by identifying cytogenetically or molecularly a clonal expansion of a hematopoietic stem cell possessing a reciprocal translocation between chromosomes 9 and 22. Chromosomal analysis of the leukemic cell currently provides the most important pretreatment prognostic information in AML.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Combination Therapy

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

Chemotherapeutic agents that can be administered in combination with an anti-CD47 agent include, without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Targeted therapeutics that can be administered in combination with an anti-CD47 agent may include, without limitation, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt), IDH inhibitors, such as AG-221, PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar).

An anti-CD47 agent may be administered in combination with an immunomodulator, such as a cytokine, a lymphokine, a monokine, a stem cell growth factor, a lymphotoxin (LT), a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), such as TGF-α or TGF-β, insulin-like growth factor (IGF), erythropoietin, thrombopoietin, a tumor necrosis factor (TNF) such as TNF-α or TNF-β, a mullerian-inhibiting substance, mouse gonadotropin-associated peptide, inhibin, activin, vascular endothelial growth factor, integrin, granulocyte-colony stimulating factor (G-CSF), granulocyte macrophage-colony stimulating factor (GM-CSF), an interferon such as interferon-α, interferon-β, or interferon-γ, S1 factor, an interleukin (IL) such as IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 or IL-25, LIF, kit-ligand, FLT-3, angiostatin, thrombospondin, endostatin, and LT.

Tumor specific monoclonal antibodies that can be administered in combination with an anti-CD47 agent may include, without limitation, gemtuzumab ozogamicin (Myelotarg), Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

Of particular interest are hypomethylating (also known as epigenetic) agents for combination with an anti-CD47 agent. A hypomethylating agent is a drug that inhibits DNA methylation. Currently available hypomethylating agents block the activity of DNA methyltransferase (DNA methyltransferase inhibitors/DNMT inhibitors). Currently two members of the class, azacitidine and decitabine are FDA-approved for use in the United States. Guadecitabine is also of interest. Because of their relatively mild side effects, azacitidine and decitabine are particularly feasible for the treatment of older patients and patients with co-morbidities. Both drugs have remarkable activity against AML blasts with unfavorable cytogenetic characteristics.

Treatment of hematologic malignancies, e.g. leukemias, can be combined with one or more therapeutic entities. In some embodiments the additional therapeutic entity in an immune response modulator. Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

CTLA4 is expressed exclusively on T cells where it primarily regulates the amplitude of the early stages of T cell activation. CTLA4 counteracts the activity of the T cell co-stimulatory receptor, CD28. CD28 and CTLA4 share identical ligands: CD80 (also known as B7.1) and CD86 (also known as B7.2). The major physiological roles of CTLA4 are downmodulation of helper T cell activity and enhancement of regulatory T (TReg) cell immunosuppressive activity. CTLA4 blockade results in a broad enhancement of immune responses. Two fully humanized CTLA4 antibodies, ipilimumab and tremelimumab, are in clinical testing and use. Clinically the response to immune-checkpoint blockers is slow and, in many patients, delayed up to 6 months after treatment initiation.

Other immune-checkpoint proteins are PD1 and PDL1. Antibodies in current clinical use against these targets include nivolumab and pembrolizumab. The major role of PD1 is to limit the activity of T cells in peripheral tissues at the time of an inflammatory response to infection and to limit autoimmunity. PD1 expression is induced when T cells become activated. When engaged by one of its ligands, PD1 inhibits kinases that are involved in T cell activation. PD1 is highly expressed on $T_{Reg}$ cells, where it may enhance their proliferation in the presence of ligand. Because many tumors are highly infiltrated with $T_{Reg}$ cells, blockade of the PD1 pathway may also enhance antitumor immune responses by diminishing the number and/or suppressive activity of intratumoral $T_{Reg}$ cells.

Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine A2a receptor (A2aR) and the family of killer inhibitory receptors have each been associated with the inhibition of lymphocyte activity and in some cases the induction of lymphocyte anergy. Antibody targeting of these receptors can be used in the methods of the invention.

TIM3 inhibits T helper 1 ($T_H1$) cell responses, and TIM3 antibodies enhance antitumor immunity. TIM3 has also been reported to be co-expressed with PD1 on tumor-specific CD8$^+$ T cells. Tim3 blocking agents can overcome this inhibitory signaling and maintain or restore anti-tumor T cell function.

BTLA is an inhibitory receptor on T cells that interacts with TNFRSF14. BTLA$^{hi}$ T cells are inhibited in the presence of its ligand. The system of interacting molecules is complex: CD160 (an immunoglobulin superfamily member) and LIGHT (also known as TNFSF14), mediate inhibitory and co-stimulatory activity, respectively. Signaling can be bidirectional, depending on the specific combination of interactions. Dual blockade of BTLA and PD1 enhances antitumor immunity.

A2aR, the ligand of which is adenosine, inhibits T cell responses, in part by driving CD4$^+$ T cells to express FOXP3 and hence to develop into $T_{Reg}$ cells. Deletion of this receptor results in enhanced and sometimes pathological inflammatory responses to infection. A2aR can be inhibited either by antibodies that block adenosine binding or by adenosine analogues.

Agents that agonize an immune costimulatory molecule are also useful in the methods of the invention. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages. One of the major effects of CD47 blocking agents is to enhance phagocytosis of target cells by macrophages and other phagocytes. Therefore, combining agonistic CD40 ligands with anti CD47 can enhance the therapeutic efficacy compared to each mono therapy (example 1). Agonistic CD40 agents may be administered substantially simultaneously with anti-CD47 agents; or may be administered prior to and concurrently with treatment with anti-CD47 to pre-activate macrophages.

Agents that alter the immune tumor microenvironment are useful in the methods of the invention. Such agents include IDO inhibitors which inhibit the production of indoleamine-2,3-dioxygenase (IDO), an enzyme that exhibits an immunosuppressive effect.

Other immuno-oncology agents that can be administered in combination with CD47 blockade according to the methods described herein include antibodies specific for chemokine receptors, including without limitation anti-CCR4 and anti-CCR2. Anti CCR4 (CD194) antibodies of interest include humanized monoclonal antibodies directed against C-C chemokine receptor 4 (CCR4) with potential anti-inflammatory and antineoplastic activities. Exemplary is mogamulizumab, which selectively binds to and blocks the activity of CCR4, which may inhibit CCR4-mediated signal transduction pathways and, so, chemokine-mediated cellular migration and proliferation of T cells, and chemokine-mediated angiogenesis. In addition, this agent may induce antibody-dependent cell-mediated cytotoxicity (ADCC) against CCR4-positive T cells. CCR4, a G-coupled-protein receptor for C-C chemokines such MIP-1, RANTES, TARC and MCP-1, is expressed on the surfaces of some types of T cells, endothelial cells, and some types of neurons. CCR4, also known as CD194, may be overexpressed on adult T-cell lymphoma (ATL) and peripheral T-cell lymphoma (PTCL) cells.

The combination therapy described above may be combined with other agents that act on regulatory T cells, e.g. anti-CTLA4 Ab, or other T cell checkpoint inhibitors, e.g. anti-PD1, anti-PDL1 antibodies, and the like.

In some embodiments, administration of a combination of agents of the invention is combined with an effective dose of an agent that increases patient hematocrit, for example erythropoietin stimulating agents (ESA). Such agents are known and used in the art, including, for example, Aranesp® (darbepoetin alfa), Epogen®/Procrit® (epoetin alfa), Omontys® (peginesatide), Procrit®, etc. See, for example, U.S. Pat. No. 9,623,079.

Methods

The administration of a therapeutically effective dose of an anti-CD47 agent is provided in a schedule that provides safe escalation of dose while achieving a therapeutic level in a clinically effective period of time. The methods can comprise the steps of clearance, escalation, and maintenance. In one embodiment the dosing regimen administers an initial (i) sub-therapeutic dose of an anti-CD47 agent or (ii) a cytoreductive therapy to achieve a safe level of circulating tumor cells for subsequent treatment (clearance); escalating the dose of an anti-CD47 agent until a therapeutic dose is reached (escalation); and maintaining the therapeutic dose for a period of time sufficient to reduce tumor cells in the bone marrow of the patient (maintenance).

In an alternative dosing regimen, a patient determined to have a safe level of circulating tumor cells at presentation is treated by the steps of escalation and maintenance, comprising: escalating the dose of an anti-CD47 agent until a therapeutic dose is reached, in which greater than about 80% receptor occupancy is achieved in bone marrow blast cells from the patient (escalation); and maintaining the therapeutic dose for a period of time sufficient to reduce tumor cells in the bone marrow of the patient (maintenance).

Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., and the like.

Kits

Also provided are kits for use in the methods. The subject kits include an anti-CD47 agent. In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

CD47 is highly expressed on human acute myeloid leukemia (AML) stem cells and other cancer cells. It inhibits phagocytosis of cancer cells by human macrophages. Blocking CD47 enables macrophages to eliminate AML and through phagocytosis. Therefore, CD47 is a therapeutic antibody target. CD47-binding agents cause elimination of leukemia and other cancer cells, or other diseased cells. If a subject has a high burden of circulating diseased cells, e.g. circulating leukemia or lymphoma cells, the CD47 binding agents can cause agglutination and/or lysis but also other cell killing and elimination of the diseased cells that could lead to a potentially life threatening toxicity of the CD47 targeting therapies. Thus a dosing strategy is required that prevents acute life threatening side effects. We have established an intra-subject dose escalation strategy that prevents these toxicities by lowering the burden of circulating disease through gradually increasing the dose of CD47 targeting therapies.

We have established a human AML xenograft mouse model to test CD47-SIRPalpha pathway blocking therapies. We found that in mice xenografted with AML cells that subsequently exhibited very high burden of circulating AML cells (>50% of total white blood cell count) and marrow infiltration with AML (>90%), CD47 targeted therapy with anti-CD47 antibody (Hu5F9-G4) often caused death within 1 hour of administration of the first dose. Remarkably, early death could be prevented in these mice if low doses of Hu5F9-G4 were used at first to reduce the amount of circulating AML cells in the blood before administration of higher subsequent doses of the drug. This intra-subject dose escalation not only prevented early mortality but also resulted in safe clearance of leukemic cells.

Intra-Subject Dose Escalation (1) prevents the early death syndrome by initial treatment with low doses of anti-CD47 Ab, (2) can reduce or clear the peripheral blood of leukemia cells by initial treatment with low doses of anti-CD47 Ab or a cytoreductive agent, (3) saturates normal and leukemic cells at low doses of anti-CD47 Ab to prevent and/or reduce cell aggregation and associated toxicities and (4) enables safe administration of higher subsequent doses that can ultimately clear the disease from the blood and bone marrow. Thus, initial low doses of anti-CD47 Ab can clear the peripheral blood and facilitate administration of higher, therapeutic doses.

Example 2

Combination Treatment with Azacitidine and Hu5F9-G4 Enhances Phagocytic Elimination of Acute Myelogenous Leukemia Cancer Cells by Human Macrophages The combination of Azacitidine with Hu5F9-G4 was evaluated for the treatment of AML. Azacitidine (Vidaza©) is a chemotherapy agent that is being used for the treatment of acute myelogenous leukemia (AML). Azacitidine's anticancer effects are believed to be attributed to demethylation or interfering with the methylation of deoxyribonucleic acid (DNA), as well as interference in cellular metabolism, so as to produce a direct cytotoxic effect that causes death of rapidly dividing cancer cells.

Acute promyelocytic leukemia cells (HL60) that have been previously transduced with a green fluorescent protein (GFP) encoding lentivirus were incubated for 24 hours with increasing doses of Azacitidine at concentrations of 0 µM, 1 µM, 3 µM, and 15 µM. HL60 leukemia cells were afterwards co-cultured for 2 hours with human macrophages, derived from human monocytes, in the presence or absence of Hu5F9-G4 Ab at a concentration of 10ug/ml. Macrophages were labeled with an anti-CD206 Ab and all cells were analyzed by flow cytometry to determine phagocytosis of HL60 leukemia cells. Phagocytosis of HL60 leukemia cells was determined as percentage of GFP positive, HL60 engulfing, macrophages compared to total number of macrophages. Results were normalized to the condition with maximal phagocytosis (100%).

The combination of azacitidine at a concentration of 3 µM with Hu5F9-G4 enhanced the phagocytic elimination of HL60 leukemia cells by human macrophages compared to the phagocytosis of HL60 leukemia cells that have only been treated with a single agent: azacitidine or Hu5F9-G4. The 3 µM azacitidine dose was selected since this is the approximate peak plasma concentration of azacitidine in patients. Azacitidine at a concentration of 1 µM did not enhance the phagocytic elimination of HL60 leukemia cells. Azacitidine at a concentration of 15 µM in combination with Hu5F9-G4 did not enhance the phagocytic elimination of HL60 leukemia cells more than azacitidine at a concentration of 3 µM. These results were consistent across two different assays with macrophages derived from two different monocyte donors.

In summary, the combination of azacitidine at a concentration of 3 µM with Hu5F9-G4 significantly enhanced the phagocytic elimination of HL60 leukemia cells by human macrophages in vitro compared to single agent treatment with azacitidine or Hu5F9-G4. These experiments provide a preclinical demonstration of efficacy for a combination of Hu5F9-G4 and azacitidine in AML patients.

Clinically, Hu5F9-G4 may be combined with azacitidine, decitabine, or other hypomethylating agent for the treatment of 1) treatment naïve AML patients who are ineligible for standard induction chemotherapy or allogeneic hematopoietic cell transplant due to age and/or co-morbidities; 2) relapsed and/or refractory AML patients either to first line hypomethylating agent or standard therapies; 3) previously untreated intermediate and high risk myelodysplastic syndrome (MDS) patients; and 4) MDS patients who are relapsed and/or refractory to frontline hypomethylating agents.

This study demonstrates that the combination of azacitidine with Hu5F9-G4 can enhance the phagocytic elimination of HL60 leukemia cells by human macrophages in vitro compared to single agent treatment with Azacitidine or Hu5F9-G4.

Example 3

Hu5F9-G4 Dose Escalation Treatment Prevents Acute Death in Mice with High Disease Burden In this study, a dose escalation regimen was investigated as a preventive strategy for early death induced by Hu5F9-G4, a humanized anti-CD47 antibody, against human AML disease in a mouse xenograft model. In a prior study, we observed that initial therapeutic doses of Hu5F9-G4 caused early death in AML engrafted mice. We also observed that early death seemed to be related to burden of circulating disease, in that mice with high levels of circulating leukemia cells succumbed to early death. We hypothesized that initial low doses of Hu5F9-G4 might be able to clear circulating disease and then facilitate administration of higher, therapeutic doses to clear the bone marrow.

In xenografted mice with very high circulating leukocytes (>50% of total white blood cell count) and marrow infiltration with AML (>80%), Hu5F9-G4 treatment caused death within 1 hour of administration of the first dose. The object of this study was to determine whether early death observed in AML-xenografted mice can be avoided by reducing the rate at which leukemia cells are killed. Extensive clinical pathology and histologic analyses failed to definitively identify a cause of death. It was hypothesized that early death might be due either to agglutination of leukemic cells or tumor lysis, and that early death may be avoided by reducing the rate at which leukemia cells are killed.

To test the latter hypothesis, mice were treated with initial doses of Hu5F9-G4 ranging from 1 µg to 100 µg. Four of five mice treated with 100 µg of Hu5F9-G4 died, as did 1 of 5 mice treated with 10 μg of Hu5F9-G4; however, no early deaths were observed in 5 of 5 mice treated with 1 μg of Hu5F9-G4.

Figure 2:
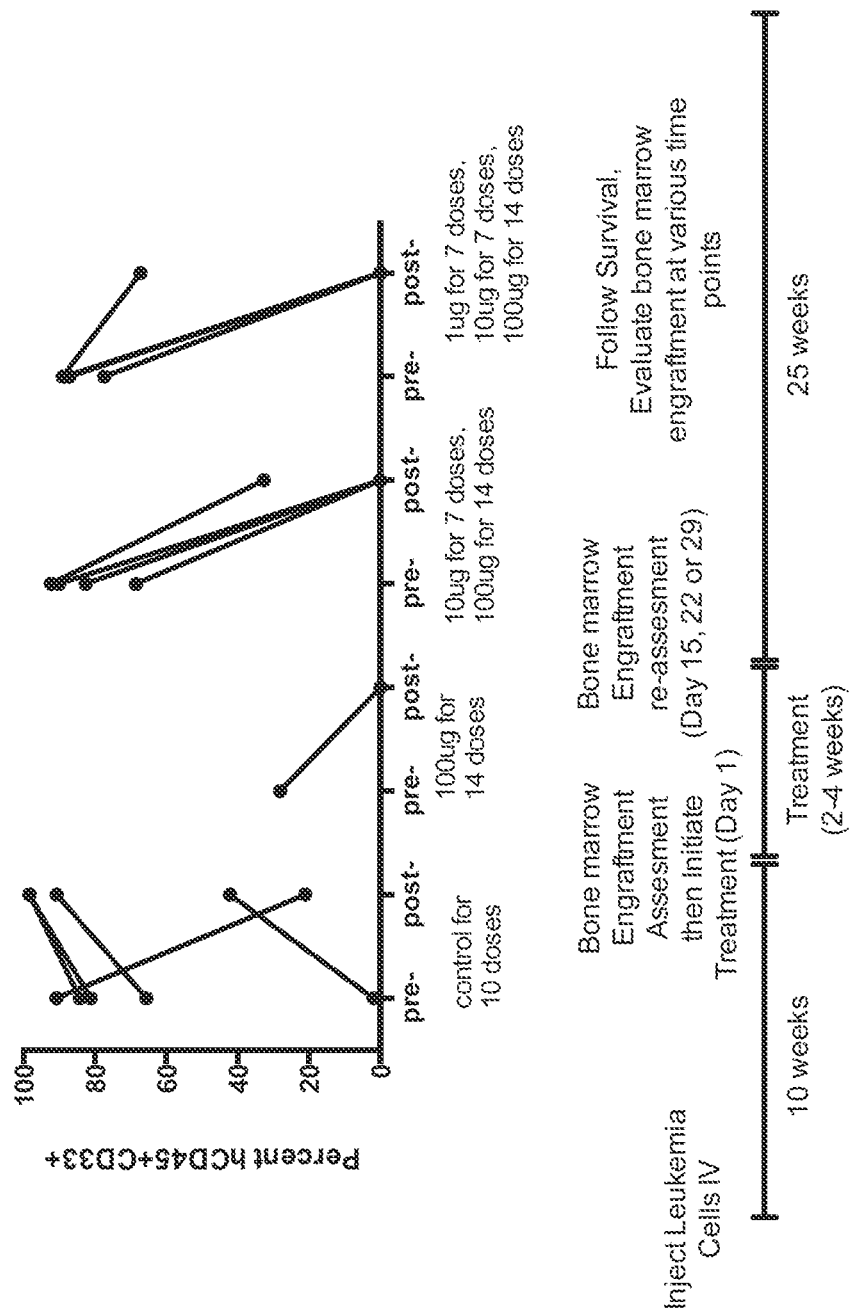
FIG. 2. Dose Escalation Treatment in AML
Figure 3B:
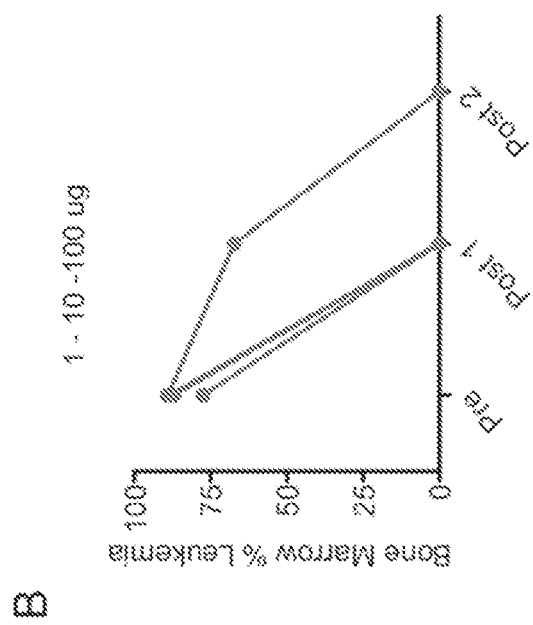
FIG. 3A-3B. Dose Escalation Treatment in AML Prevents Acute Death
Figure 3A:
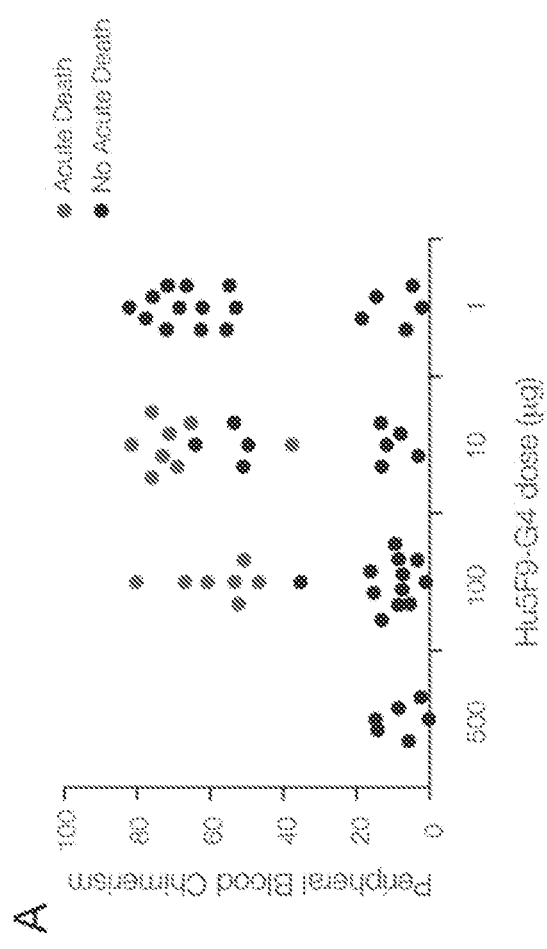
Figure 4:
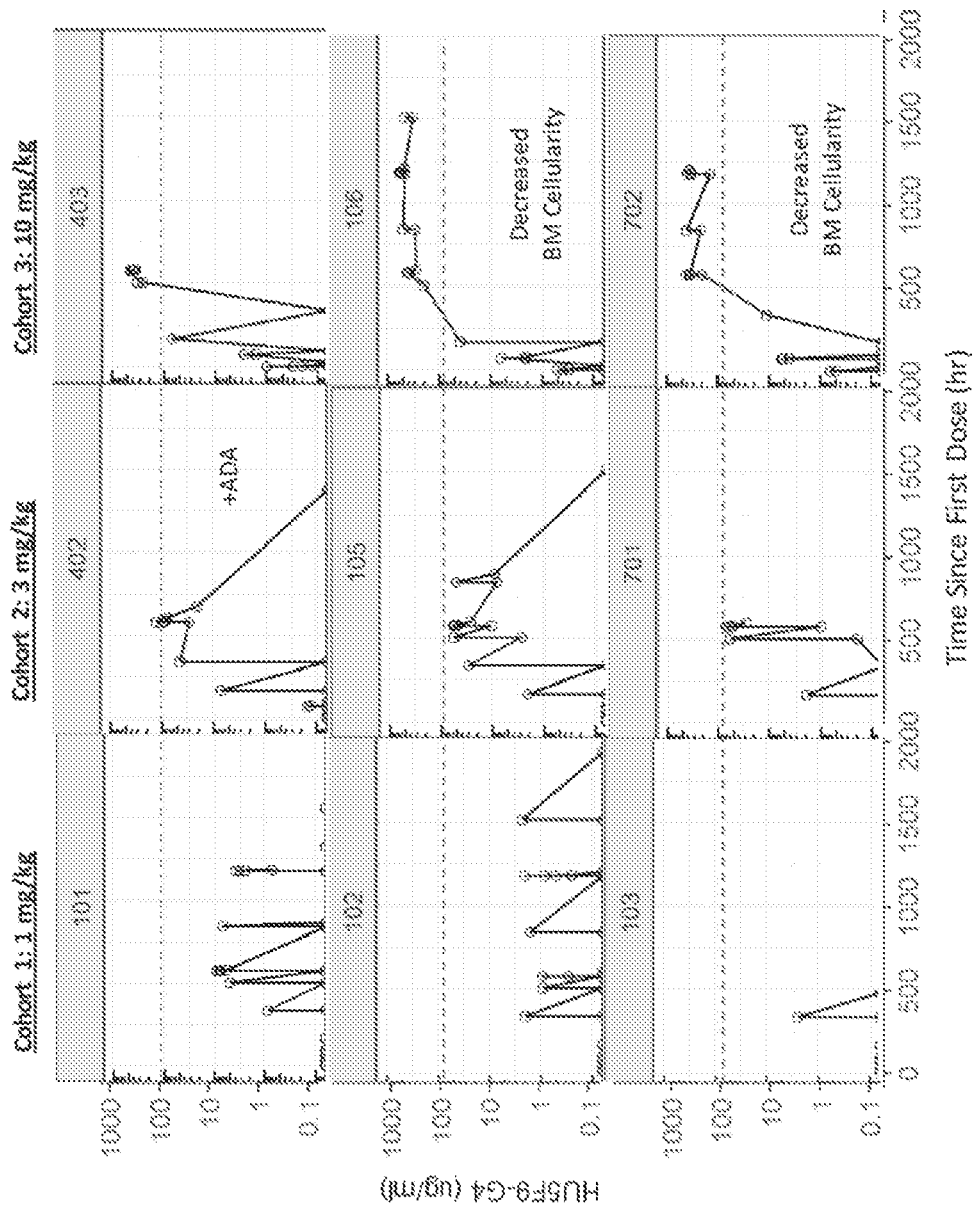
FIG. 4. Patient Serum Concentrations of Hu5F9-G4.
Figure 6:
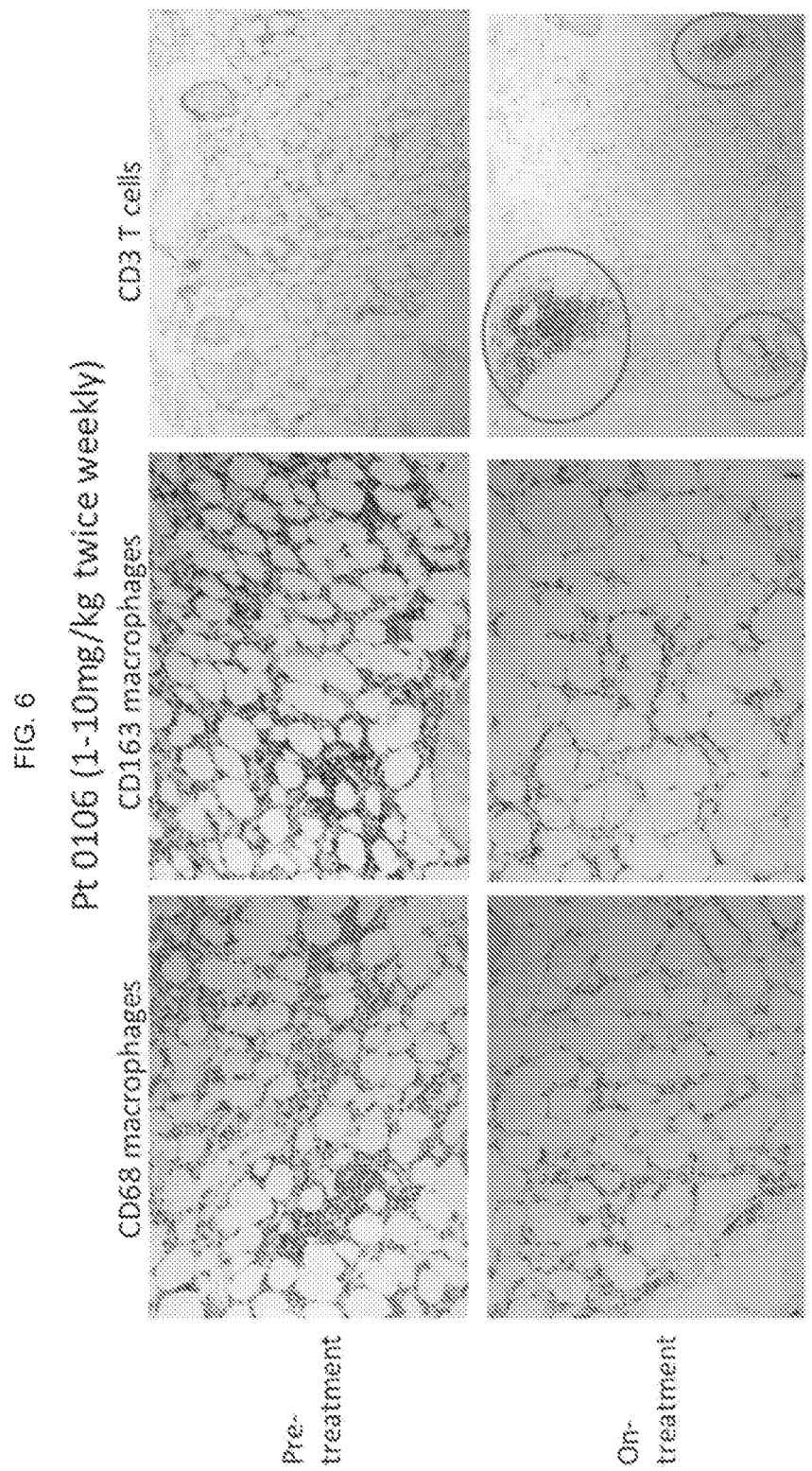
FIG. 6. Photomicrographs of Immunohistochemistry Analysis for Macrophages and T Cells in Bone Marrow Biopsies from Patients Treated with Hu5F9-G4

To determine whether using low initial doses of Hu5F9-G4 could safely reduce disease, after which higher doses could be used to cure disease, surviving mice from the same study continued dosing. Mice were treated with following Hu5F9-G4 dosing schemes: Cohort I—100 μg/day for 14 days, Cohort II—10 μg/day for 7 days followed by 100 μg/day for 14 days, and Cohort III—1 μg/day for 7 days followed by 10 μg/day for 7 days followed by 100 μg/day for 14 days. Four out of five mice in Cohort I, injected with initial dose of 100 μg of Hu5F9-G4 experienced early death syndrome. The sole surviving mouse tolerated the remaining 14 doses of 100 μg of antibody and disease was cleared. One mouse out of five in Cohort II that received an initial dose of 10 μg of Hu5F9-G4 experienced early death; the remaining four mice survived first seven doses of 10 μg of Hu5F9-G4 and subsequent 14 doses of 100 μg. None of the mice in Cohort III that received an initial dose of 1 μg of Hu5F9-G4 experienced early death; however, clearance of disease was noticeably diminished after 7 doses of 1 μg, 7 doses of 10 μg, and 14 doses of 100 μg and mice relapsed several weeks after the end of treatment. All mice in the control group continuously progressed and died. Groups that received dose-escalating regimen of Hu5F9-G4 had increased burden of disease and AML cells and relapsed after stop of initial treatment. Retreatment cleared the disease and led to long-term disease free survival in some cases. Results are shown in FIGS. 2 and 3.

Example 4

Pharmacokinetic and Efficacy Profile in AML

Given the widespread expression of CD47 on normal tissues, a therapeutic Hu5F9-G4 dose must be able to saturate the internal CD47 sink in order to saturate and eliminate leukemic cells. In the AML Phase 1 trial, it is demonstrated that the Hu5F9-G4 dosing regimen is able to saturate the internal CD47 sink and lead to meaningful circulating drug levels at clinically feasible dosing.

In pre-clinical models, it was determined that an Hu5F9-G4 trough level of 100 μg/ml or higher was associated with efficacy (dotted blue line). This trough level served as the minimum trough level target to guide dosing in the Phase 1 trial. Dose levels 3 mg/kg or less did not achieve target trough levels. Rapid peaks and troughs observed were consistent with target-mediated disposition due to non-linear saturation of the CD47 sink. Response to therapy was therefore not expected nor observed at or below a concentration of 3 mg/kg (Cohorts 1 and 2). Dose levels of 10 mg/kg or greater (Cohorts 3 and 4) achieve target trough levels by about 4 weeks, which is the time of first response assessment.

Example 5

Therapeutic Effect of Hu5F9-G4 Treatment in AML

In patients receiving a maximum of 10 mg/kg Hu5F9-G4 twice weekly (Cohort 3), two out of three patients (106 and 702) exhibited biologic antileukemic activity. These two patients exhibited markedly hypocellular bone marrow and absolute blast count reduction similar to Hu5F9-G4 anti-leukemic activity observed in preclinical murine xenograft models. Several additional factors are notable for these patients with biologic activity. First, one of these two patients exhibited a partial response (PR) with a >50% blast reduction, with a durable response over 6 months and ongoing. Clinically this patient has tolerated therapy well and has had a significant improvement in RBC transfusion requirements from approximately every week prior to treatment to once a month during month 3 and beyond of treatment.

CD47 receptor occupancy on leukemic blasts in the bone marrow have been measured in all patients as a pharmacodynamic measure of Hu5F9-G4 activity. In these two patients with biologic response, 50-60% CD47 receptor occupancy on leukemic bone marrow cells has been observed, demonstrating tumor cell engagement by Hu5F9-G4.

Based on the MOA of Hu5F9-G4 in inducing macrophage and T cell specific anti-leukemic activity, the presence of immune effector cells in the tumor microenvironment (bone marrow) was assessed in this patient with durable response. Despite significant hypocellularity induced by Hu5F9-G4, a significant number of macrophages (assessed by either CD68 or CD163 staining) were present in the marrow at week 4 of treatment. Furthermore, T cell infiltration into the bone marrow markedly increased during treatment: 10-15% T cell infiltrates were present at baseline with an increase to 40-50% of all bone marrow cells by week 8 of therapy (blue circles). While sample size is limited, this data suggests that Hu5F9-G4 eliminates leukemic cells through both innate and adaptive immune mechanisms as demonstrated in pre-clinical studies.

Figure 9:
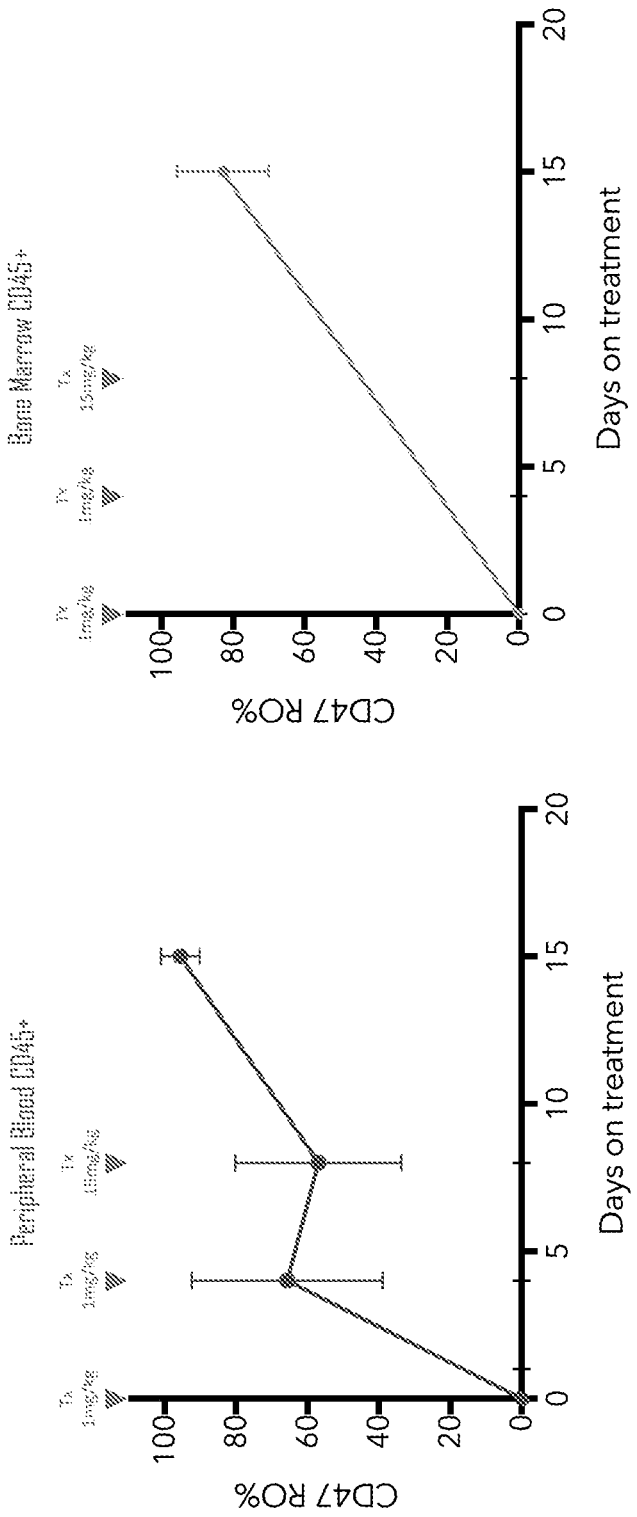
FIG. 9. CD47 receptor occupancy in AML. The data show that one dose of 15 mg/kg (after the priming doses of 1 mg/kg) was sufficient to achieve nearly 100% RO in the critical compartments of peripheral blood and bone marrow.

As shown in FIG. 9, a patient was treated with a priming dose of 5F9-G4 of 1 mg/kg at day 1 and day 4. The dose was escalated to 15 mg/kg at day 8. The receptor occupancy was measured following each administration. For $CD45^+$ peripheral blood and bone marrow, this dosing provided for nearly complete receptor occupancy.

Example 6

Combination Therapy with Cytoreduction Agents and Hu5F9-G4

Co-treatment with cytoreductive therapies and Hu5F9-G4 to reduce circulating leukemic cell burden can mitigate the risk of early death associated with Hu5F9-G4. Cytoreductive therapies are agents that reduce the circulating and bone marrow tumor burden and includes therapies such as hydroxyurea, oral etoposide, leukapheresis, and other cytotoxic chemotherapies. In pre-clinical models, the impact of hydroxyurea and potential additive toxicity with ongoing Hu5F9-G4 treatment was assessed in immune competent wild type healthy mice.

In a Phase 1 trial of Hu5F9-G4 in relapsed/refractory AML, cytoreduction with either hydroxyurea and/or oral etoposide was utilized to reduce the circulating WBC burden to $<10 \times 10^9$/L during concomitant dosing of Hu5F9-G4. The addition of hydrea with Hu5F9-G4 treatment was sufficient to maintain patients' WBC$<10 \times 10^9$/L while on trial without increased toxicities. No acute death related to Hu5F9-G4 was observed on any patients treated on trial as of this patent submission.

Example 7

Immuno-Oncology Therapy Combinations with Hu5F9-G4

Blockade of the CD47-SIRPα signaling axis on tumor cells by a monoclonal blocking anti-CD47 antibody leads to tumor elimination by activation of both the innate and adaptive immune system. Anti-CD47 antibody-mediated tumor elimination by the innate immune system occurs through phagocytic elimination of tumor cells by macrophage and other phagocytes. It is well known that macrophages are a common immune cell infiltrate in many tumor types, with degree of intratumoral macrophage infiltrate correlating with clinical prognosis. Correlation of macrophage infiltration to clinical disease course is often dependent on the presence of either classically activated (M1) type macrophages that suppress tumor progression or alternatively, activated (M2) type macrophages that promote tumor progression.

Given the frequent infiltration of M2 macrophages in many tumor types and its role in promoting tumorigenesis, there is widespread interest in developing therapies that shift tumor macrophage polarization from the pro-tumorigenic M2 to the anti-tumorigenic M1 macrophages. In nonclinical studies, anti-CD47 antibody-mediated tumor cell phagocytosis has been demonstrated to occur through both M1 and M2 macrophages (see Zhang et al. (2016) PLoS ONE 11(4): e0153550). In addition, in vivo treatment of human xenograft tumors with an anti-CD47 antibody demonstrated increased M1 intratumoral macrophages post-treatment, suggesting that an anti-CD47 antibody can also shift the phenotype of macrophages from the M2 towards the M1 phenotype in vivo. Since the recruitment of macrophage effectors is a key mechanism for anti-tumor activity by anti-CD47 antibody, the characterization of macrophage tumor infiltration pre- and post-treatment in patients treated with anti-CD47 antibody provide insights into patient and cancer subtypes and macrophage biomarkers that will enrich for anti-tumor efficacy.

In addition to modulating the innate immune system, anti-CD47 antibody therapy also activates the adaptive immune system towards an anti-tumor response. Phagocytosis of tumor cells by phagocytes (macrophages and/or dendritic cells) leads to cross-presentation of tumor antigens to T cells, enabling a T-cell anti-tumor response. In one nonclinical study, anti-CD47 antibody mediated a specific CD8 T-cell anti-tumor response without proliferation of regulatory T cells (which are generally thought to be tumor-promoting). Currently, there is intense interest in investigating the relationship between T-cell subsets that infiltrate the tumor and clinical response with the use of immune-oncology therapeutics. Indeed, increased T-cell infiltration in the tumor has been associated with clinical response in oncology patients treated with T-cell checkpoint inhibitors. Given the role of anti-CD47 antibody in mediating an anti-tumor T-cell response, the clinical investigation of the contribution of T-cell effectors to anti-CD47 antibody-mediated efficacy is important to select for patients and tumor subtypes that respond to therapy.

Based on the MOA of Hu5F9-G4 in inducing macrophage and T cell specific anti-leukemic activity, the presence of immune effector cells in the tumor microenvironment (bone marrow) was assessed in patients with AML on the Phase 1 clinical trial with Hu5F9-G4. In one patient that obtained a partial response, macrophage and T cell infiltrates in the bone marrow was assessed.

A significant number of macrophages (assessed by either CD68 or CD163 staining) were present in the marrow at week 4 of treatment. Furthermore, T cell infiltration into the bone marrow markedly increased during treatment: 15% T cell infiltrates were present at baseline with an increase to 40-50% of all bone marrow cells by week 8 of therapy (blue circles). This data indicates that Hu5F9-G4 eliminates leukemic cells through both innate and adaptive immune mechanisms as demonstrated in pre-clinical studies.

Based on evidence of increased T cell tumor infiltrates with Hu5F9-G4 treatment, the combination of therapeutic agents that activate and enhance an anti-tumor T cell response with Hu5F9-G4 can lead to enhanced clinical efficacy. Combination treatment with Hu5F9-G4 includes T cell checkpoint inhibitors (e.g. anti-PD1, anti-PDL1, anti-CTLA-4, anti-Tim3 antibodies).

Example 8

Biomarkers

The use of molecular, cytogenetic, immunophenotypic, and tumor microenvironment profiling to select patients with leukemia or pre-leukemic conditions (e.g. MDS) that predict an enhanced clinical response to Hu5F9-G4.

In pre-clinical models, Hu5F9-G4 has demonstrated monotherapy activity across a wide range of cytogenetic, molecular, and phenotypic AML subtypes. However, Hu5F9-G4 treatment may have preferentially enhanced clinical activity in certain AML subtypes. Prospective testing of AML patients' molecular, chromosomal, and phenotypic characteristics by DNA sequencing, cytogenetic analysis/fluorescence in situ hybridization (FISH), and flow cytometry, can lead to identification of patients with greater responses to Hu5F9-G4. In the Phase 1 AML trial, targeted DNA sequencing of myeloid mutations was performed on patients receiving Hu5F9-G4 treatment. Reduction in mutational burden (variant allele frequency) was observed for some mutations over others.

In addition to AML phenotypic selection, prospective characterization of the tumor microenvironment in the bone marrow may be predictive of Hu5F9-G4 response. Given that macrophages, other phagocytes, and T cells are primary effector cells required for Hu5F9-G4 anti-tumor activity, the frequency of these immune cell types in the bone marrow prior to treatment may be predictive of Hu5F9-G4 activity. Specifically, increased macrophage frequency in the bone marrow by CD68, CD163, M1 and M2 characterization, and other similar markers may be correlated with enhanced efficacy. Increased neutrophil, dendritic cell, and T cell infiltration may also be correlated with enhanced efficacy. Specific T cell subtypes, including but not limited to characterization of CD3, CD4, CD8, PDL1, PD1, FoxP3, CD25 expression may correlate with Hu5F9-G4 efficacy. Lastly, the degree of SIRPα infiltration in the tumor may be predictive of response since SIRPα is the ligand to CD47 on effector cells. The modalities of immune effector characterization in the bone marrow would include immunohistochemistry, immunofluorescence, cyTOF, and flow cytometry.

Example 9

Hu5F9-G4 Aml Indications

Hu5F9-G4 has broad pre-clinical activity across AML morphologic, molecular, and cytogenetic subtypes. Thus, Hu5F9-G4 may have broad potential clinical activity in AML. With regards to specific clinical indications, Hu5F9-G4 may be treated in: 1) Relapsed and/or refractory acute myeloid leukemia; 2) AML patients who are ineligible for standard induction chemotherapy who failed standard low intensity therapy (e.g. with hypomethylating agents); 3)

AML patients in morphologic complete remission with evidence of minimal residual disease.

Minimal residual disease (MRD) monitoring has become a powerful prognostic factor that is beginning to play a central role in the treatment of AML patients both in the pre- and post-transplant setting. In multiple large studies of newly diagnosed AML patients, MRD positivity post-therapy was an independent poor prognostic factor and predictor of relapse. In addition, MRD positivity also appears to be a poor prognostic factor in the post-transplant setting. In a retrospective study, patients with morphologic remission undergoing allogeneic HSCT, the presence of MRD prior to transplant was an independent predictor of relapse as 67% of patients with MRD-positive remission relapsed within 3 years post-transplant as compared to 22% in MRD-negative remission. Several methods for MRD monitoring have been utilized in AML including 1) multi-parameter flow cytometry for detection of aberrant hematopoietic surface antigens; 2) molecular monitoring of leukemia-specific mutational burden; 3) cytogenetic monitoring of leukemia-associated chromosomal abnormalities.

In pre-clinical and initial clinical studies, Hu5F9-G4 has demonstrated enhanced activity in lower tumor burden of disease. Thus, Hu5F9-G4 can be more efficacious in settings where minimal tumor burden is detected, especially in patients with minimal residual disease.

Example 10

Assay for Receptor Occupancy

A schematic for the assay is provided in FIG. 7. Patient peripheral blood and bone marrow aspirates are collected at scheduled time points (e.g. day 1 pre-Hu5F9-G4 dosing, day 1 post-Hu5F9-G4, etc). These samples are split into two tubes, "$RO_{test}$" and "$RO_{saturated}$". "$RO_{saturated}$" are artificially saturated ex vivo with 200 µg/ml of Hu5F9-G4 in order to simulate 100% receptor occupancy (previously determined to saturate). $RO_{test}$ are not artificially saturated. These two tubes are then stained with 200 µg/ml of an AlexaFlour-647 conjugated anti-IgG4 (clone G17-4) to determine the fluorescent intensity on red blood cells and white blood cells, including blasts. Receptor occupancy of each blood fraction will be determined as the percentage ratio of the $RO_{test}$ median fluorescent intensity (MFI) divided by the $RO_{saturated}$ MFI.

Example 11

An exemplary clinical dosing protocol is provided in FIG. 8. The upper table provides lower dosing ranges for phase 1 clinical trial use, and the lower table provides clinically relevant dosing schedules.

What is claimed is:

1. A method of treating a patient for Myelodysplastic Syndrome (MDS), the method comprising: administering to said patient an effective dose of Hu5F9-G4, in combination with an effective dose of azacitidine.

2. The method of claim 1, wherein Hu5F9-G4 is administered to said patient in an initial dose of 1 mg/kg/dose.

3. The method of claim 1, wherein Hu5F9-G4 is administered to said patient in successive doses escalated by 1 to 30 mg/kg/dose.

4. The method of claim 1, wherein Hu5F9-G4 is administered to said patient in successive doses escalated by 15 mg/kg/dose.

5. The method of claim 1, wherein a maintenance dose of Hu5F9-G4 is 30 mg/kg.

6. The method of claim 1, wherein the Hu5F9-G4 dose is escalated semi-weekly to bi-weekly.

* * * * *